United States Patent [19]
Wilk

[11] Patent Number: 5,284,159
[45] Date of Patent: Feb. 8, 1994

[54] PROPHYLACTIC DEVICE

[76] Inventor: Peter J. Wilk, 185 W. End Ave., New York, N.Y. 10023

[21] Appl. No.: 986,282

[22] Filed: Dec. 7, 1992

Related U.S. Application Data

[63] Continuation-in-part of Ser. No. 816,461, Jan. 3, 1992, Pat. No. 5,191,902.

[51] Int. Cl.⁵ .................................................. A61F 6/04
[52] U.S. Cl. ..................... 128/844; 128/842; 128/918; 604/349
[58] Field of Search ............ 128/842, 844, 918; 604/327, 328, 329, 330, 331, 346, 347, 349

[56] References Cited

U.S. PATENT DOCUMENTS

| | | |
|---|---|---|
| 2,577,345 | 12/1951 | McEwen ........................ 128/844 |
| 2,586,674 | 2/1952 | Lonne . |
| 4,638,790 | 1/1987 | Conway et al. . |
| 4,798,600 | 1/1989 | Meadows . |
| 4,898,184 | 2/1990 | Skurkovich et al. . |
| 4,910,803 | 3/1990 | Cukier . |
| 4,919,149 | 4/1990 | Stang . |
| 4,930,522 | 6/1990 | Busnel et al. . |
| 4,961,734 | 10/1990 | Kassman . |
| 4,972,849 | 11/1990 | Park et al. . |
| 4,984,582 | 1/1991 | Romaniszyn et al. . |
| 5,018,532 | 5/1991 | Etheredge, III ................. 123/844 |
| 5,050,619 | 9/1991 | Ferguson . |
| 5,193,555 | 3/1993 | Richarson et al. ............... 128/842 |

Primary Examiner—Robert A. Hafer
Assistant Examiner—Sam Rimell
Attorney, Agent, or Firm—R. Neil Sudol; Henry D. Coleman

[57] ABSTRACT

A prophylactic device comprises an outer condom having a circular base, and an inner condom inserted inside the first condom and also having a circular base. The device further comprises a heat seal attaching the outer condom and the inner condom to one another about their respective bases. The outer condom is provided in a region about its base with a plurality of openings disposed in an annular array for permitting the evacuation of air from between the first condom and the second condom during use of the device.

20 Claims, 1 Drawing Sheet

PROPHYLACTIC DEVICE

Cross-Reference to Related Application

This application is a continuation-in-part of U.S. application Ser. No. 816,461 filed Jan. 3, 1992, now U.S. Pat. No. 5,191,902.

BACKGROUND OF THE INVENTION

This invention relates to a prophylactic device. More particularly, this invention relates to an improved condom.

In this day of dreaded venereal diseases and sexual freedom, people have been increasingly urged by the medical profession, as well as by governmental organizations, to use condoms to prevent the spread of venereal diseases.

However, condoms are well known to be only partially effective. Leakage and breakage both serve to reduce the effectiveness of condoms as a barrier to contagion and to conception.

OBJECTS OF THE INVENTION

An object of the present invention is to provide an improved condom.

Another object of the present invention is to provide a condom which increases the effectiveness of the device as a barrier to the spread of disease.

Another, more particular, object of the present invention is to provide such a condom which is not prohibitively expensive.

SUMMARY OF THE INVENTION

A prophylactic device comprises, in accordance with the present invention, an outer condom and an inner condom. The outer condom is closed at an end opposite its base, while the inner condom is inserted inside the outer condom. The inner condom is open at its base and closed at an end opposite its base. The condoms are attached to one another about their respective bases, at least one of the condoms being provided along a surface facing the other condom with a series of projections for enhancing genital stimulation during intercourse.

Pursuant to another feature of the present invention, the device further comprises a lubricating substance disposed between the condoms. The lubricant may include a spermicidal agent, a bacteriocidal agent, and/or an antiviral agent.

Pursuant to a further feature of the present invention, the outer condom is provided in a region about its base with at least one opening for permitting the evacuation of air from between the condoms during use of the device. Preferably, a series of openings are angularly equispaced in a circular or annular array about the base of the outer condom.

Pursuant to an additional feature of the present invention, the outer condom is longer than the inner condom, the condoms being slidable one relative to the other during use of the device during intercourse, thereby facilitating the action of the projections.

Where the projections are provided on the outer condom, the projections may be located at least in part near the closed end of that condom.

The projections may take the form of annular ribs.

Pursuant to yet another feature of the present invention, the condoms have different colors, thereby facilitating detection of breakage or perforation of the outer condom.

Another prophylactic device comprises, in accordance with the present invention, an outer condom closed at an end opposite its base and a second, inner, condom inserted inside the outer condom. The inner condom is open at its base and is closed at an end opposite its base, while means are provided for attaching the outer condom and the inner condom to one another about their respective bases. The outer condom is provided in a region about the first base with an opening for permitting the evacuation of air from between the outer condom and the inner condom during use of the device. In addition, at least one of the condoms is provided with a high-friction surface facing the other condom, thereby serving to strengthen the device by maintaining the two condoms in a fixed relative structure.

The outer and inner condoms may be attached to one another about their respective bases via a heat seal.

An improved prophylactic in accordance with the present invention may be rolled in the manner of conventional condoms for transport and sale.

A condom in accordance with the present invention increases the effectiveness of the condom as a barrier to the spread of disease. Moreover, such a condom is not prohibitively expensive to manufacture.

DETAILED DESCRIPTION

Figure 1:
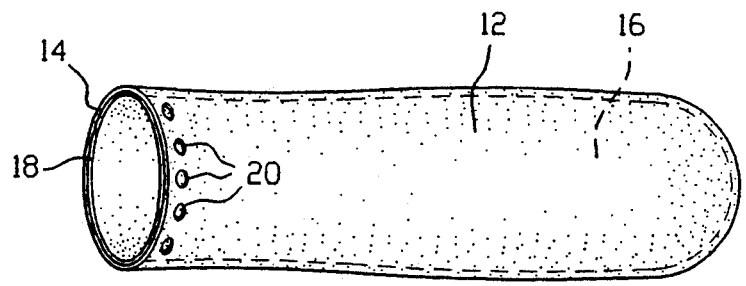
FIG. 1 is a schematic side elevational view of a prophylactic device including two condoms or sheaths inserted one inside the other.

As illustrated in FIG. 1, a prophylactic device comprises an outer condom 12 having a circular base 14 and an inner condom 16 inserted inside the outer condom. Inner condom 16 likewise has a circular base 18 defining an opening for the insertion of a penis (not illustrated). Outer condom 12 and inner condom 16 are attached to one another about their respective bases 14 and 18. In addition, outer condom 12 is provided in a region about base 14 with a plurality of openings 20 spaced from each other in an annular array for permitting the evacuation of air from between the outer condom and inner condom 16 during use of the device.

Outer condom 12 and inner condom 16 are attached to one another about their respective bases 14 and 18 via an annular heat seal.

Figure 2:
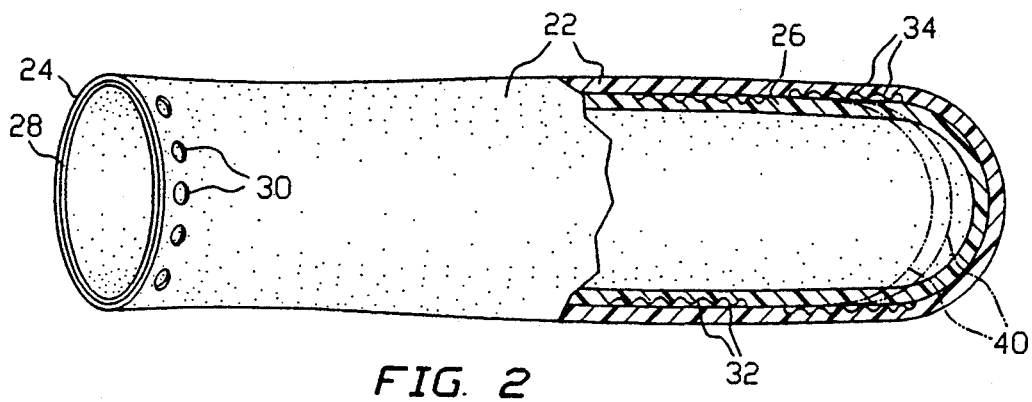
FIG. 2 is a schematic side elevational view, partially broken away and on a larger scale, of a prophylactic device in accordance with the present invention.

As illustrated in FIG. 2, a prophylactic device comprises an outer condom 22 having a circular base 24 and an inner condom 26 inserted inside the outer condom. Inner condom 26 likewise has a circular base 28 defining an opening for the insertion of a penis (not shown). Outer condom 22 and inner condom 26 are attached to one another about their respective bases 24 and 28, for example via an ultrasonic weld or heat seal. In addition, outer condom 22 is provided in a region about base 24 with a plurality of openings 30 spaced from each other in a circular or annular array for permitting the evacuation of air from between the outer condom and inner condom 26 during use of the device.

As further illustrated in FIG. 2, inner condom 26 is provided along an outer side, facing outer condom 22, with a plurality of spaced projections 32 in the form of annular ribs. Outer condom 22 is likewise provided along an inner surface, facing inner condom 26, with a plurality of spaced projections 34 in the form of annular ribs. Ribs 32 may overlap ribs 34 or may be longitudinally spaced therefrom along the length of the prophylactic device, as illustrated in FIG. 2.

Figure 4:
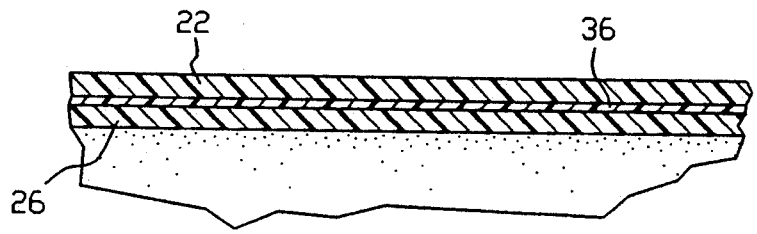
FIG. 4 is a partial cross-sectional view of a side wall of another prophylactic device in accordance with the present invention.

In one embodiment, inner condom 22 and outer condom 26 may be relatively fixed with respect to one another even during use of the device. This relative fixation may be enhanced or implemented by the provision, on an inner surface of outer condom 22 or on an outer surface of inner condom 26, of a layer 36 of high-friction material such as a tacky polymer, as depicted in FIG. 4.

In another embodiment, a lubricating substance optionally including a bactericidal agent, an antiviral agent, and/or a spermicidal agent is disposed in a space 38 (FIG. 3) between outer condom 22 and inner condom 26. In this event, as indicated in dot-dash lines 40 in FIG. 2, outer condom 22 may be longer than inner condom 26, to provide for a relative motion between the condoms or sheath layers during use of the prophylactic device. This relative motion serves to enhance the stimulation afforded the female organ by projections or ribs 32 and to enhance the stimulation afforded the male organ by projections or ribs 34.

Figure 3:
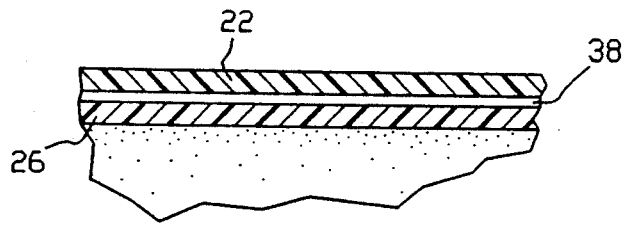
FIG. 3 is a partial cross-sectional view of a side wall of the prophylactic device of FIG. 2, showing a modification of the device.

In the embodiment of FIG. 3, i.e., where a lubricating substance is disposed in space 38, it is desirable to omit apertures 30, to prevent leakage or ejection of the lubricating substance during use of the prophylactic device. Thus, space 38 is hermetically sealed.

Condoms 12 and 16, or 22 and 26, may be of different colors, thereby facilitating detection of breakage or perforation of the outer condom.

Although the invention has been described in terms of particular embodiments and applications, one of ordinary skill in the art, in light of this teaching, can generate additional embodiments and modifications without departing from the spirit of or exceeding the scope of the claimed invention. For example, in the double condom of FIG. 2, ribs 32 or 34 may be omitted, leaving only one set of stimulation-enhancing projections. In addition, to increase the strength of the device of FIG. 1, that device may be formed with the high-friction intermediate layer or surface discussed hereinabove with reference to FIG. 4. It is to be noted in this regard that one or both condoms 12 and 16 may be made of a high-friction material.

For these reasons and others, it is to be understood that the drawings and descriptions herein are preferred by way of example to facilitate comprehension of the invention and should not be construed to limit the scope thereof.

What is claimed is:

1. A prophylactic device comprising:
   a first condom having a first base, said first condom being closed at an end opposite said first base; and
   a second condom inserted inside said first condom so as to be substantially slidable with respect to said first condom, said second condom having a second base, said second condom being open at said second base and closed at an end opposite said second base, said first condom and said second condom being attached to one another about their respective bases,
   at least one of said first condom and said second condom being provided along a surface facing the other condom with a series of projections for enhancing genital stimulation during intercourse.

2. The device defined in claim 1, further comprising a lubricating substance disposed between said first condom and said second condom.

3. The device defined in claim 2 wherein said lubricating substance is selected from a group consisting of a spermicidal agent, a bacteriocidal agent, and an antiviral agent.

4. The device defined in claim 2 wherein said lubricating substance includes a spermicidal agent.

5. The device defined in claim 2 wherein said lubricating substance includes a bacteriocidal agent.

6. The device defined in claim 2 wherein said lubricating substance includes an antiviral agent.

7. The device defined in claim 1 wherein said first condom is provided in a region about said first base with an opening for permitting the evacuation of air from between said first condom, and said second condom during use of the device.

8. The device defined in claim 7 wherein said first condom is provided with a plurality of openings in said region about said first base.

9. The device defined in claim 8 wherein said openings are spaced in an annular array at said first base.

10. The device defined in claim 1 wherein said first condom is longer than said second condom.

11. The device defined in claim 10, further comprising a lubricating substance disposed between said first condom and said second condom.

12. The device defined in claim 1 wherein said one of said first condom and said second condom is said first condom, said projections being located at least in part near the closed end of said first condom.

13. The device defined in claim 1 wherein said projections are annular ribs.

14. The method defined in claim 1 wherein said first condom and said second condom have different colors.

15. A prophylactic device comprising:
   a first condom having a first base, said condom being closed at an end opposite said base;
   a second condom inserted inside said first condom, said second condom having a second base, said second condom being open at said second base and closed at an end opposite said second base; and
   means for permanently said first condom and said second condom to one another about their respective bases, said first condom being provided in a region about said first base with an opening for permitting the evacuation of air from between said first condom and said second condom during use of the device,
   at least one of said first condom and said second condom being provided with a tacky surface facing the other of said first condom and said second condom.

16. A prophylactic device comprising:
   a first condom having a first base, said first condom being closed at an end opposite said first base; and
   a second condom inserted inside said first condom, said second condom having a second base, said second condom being open at said second base and closed at an end opposite said second base, said first condom and said second condom being permanently attached to one another about their respective bases, said first condom and said second condom have different colors.

17. The device defined in claim 16, further comprising a lubricating substance disposed between said first condom and said second condom.

18. The device defined in claim 16 wherein said first condom is provided in a region about said first base with an opening for permitting the evacuation of air from between said first condom and said second condom during use of the device.

19. The device defined in claim 18 wherein said first condom is provided with a plurality of openings in said region about said first base.

20. A prophylactic device comprising:
- a first condom having a first base, said condom being closed at an end opposite said base;
- a second condom inserted inside said first condom, said second condom having a second base, said second condom being open at said second base and closed at an end opposite said second base;
- means for permanently attaching said first condom and said second condom to one another about their respective bases, said first condom being provided in a region about said first base with an opening for permitting the evacuation of air from between said first condom and said second condom during use of the device; and
- a lubricating substance disposed between said first condom and said second condom.

* * * * *

UNITED STATES PATENT AND TRADEMARK OFFICE
CERTIFICATE OF CORRECTION

PATENT NO. : 5,284,159
DATED : February 8, 1994
INVENTOR(S) : Peter J. Wilk

It is certified that error appears in the above-indentified patent and that said Letters Patent is hereby corrected as shown below:

Column 3, Claim 1, line 10, insert -- permanently -- after "being".---

Column 4, Claim 15, line 8, insert -- attaching -- after "permanently".--

Signed and Sealed this

Nineteenth Day of July, 1994

Attest:

BRUCE LEHMAN

*Attesting Officer*          *Commissioner of Patents and Trademarks*